United States Patent
Koerner et al.

(10) Patent No.: US 8,113,204 B2
(45) Date of Patent: Feb. 14, 2012

(54) MICRODOSING DEVICE

(75) Inventors: Joachim Koerner, Uhldingen (DE);
Michael Helmlinger, Radolfzell (DE);
Holger Schuerle, Radolfzell (DE); Rene Bommer, Allensbach (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 1708 days.

(21) Appl. No.: 10/777,257

(22) Filed: Feb. 12, 2004

(65) Prior Publication Data

US 2004/0195352 A1    Oct. 7, 2004

(30) Foreign Application Priority Data

Feb. 13, 2003 (DE) .................. 103 06 683

(51) Int. Cl.
*A61M 11/00* (2006.01)
*A61M 15/00* (2006.01)
*A61M 16/00* (2006.01)
*F24J 3/00* (2006.01)
*F16K 31/02* (2006.01)
*B05B 1/08* (2006.01)

(52) U.S. Cl. ......... 128/207.14; 128/200.14; 128/200.16; 128/200.17; 128/200.21; 128/203.12; 128/203.14; 128/203.26; 128/204.13; 128/204.17; 128/204.21; 239/102.2

(58) Field of Classification Search .............. 128/200.14, 128/200.16, 200.17, 200.21, 203.12, 203.14, 128/203.26, 204.13, 204.17, 204.21; 239/4, 239/102.1, 102.2

See application file for complete search history.

(56) References Cited

U.S. PATENT DOCUMENTS

| 5,660,167 | A | 8/1997 | Ryder |
| 5,950,619 | A | 9/1999 | van der Linden et al. |
| 5,970,974 | A | 10/1999 | Van Der Linden et al. |
| 6,062,212 | A | 5/2000 | Davison et al. |
| 6,196,219 | B1 * | 3/2001 | Hess et al. ............ 128/200.21 |
| 2003/0000773 | A1 | 1/2003 | Engler et al. |

FOREIGN PATENT DOCUMENTS

EP    0 682 570    11/1995

* cited by examiner

*Primary Examiner* — Patricia Bianco
*Assistant Examiner* — Nihir Patel
(74) *Attorney, Agent, or Firm* — Flynn, Thiel, Boutell & Tanis, P.C.

(57) ABSTRACT

A microdosing device with a dosing chamber for the at least temporary reception of a liquid quantity, and with which is associated at least one discharge opening is provided. A vibrating unit in operative connection with at least one boundary surface of the dosing chamber is provided in order to vibrate the same for a discharge process, and with a delivery function unit connected to the vibrating unit for activating the latter during a delivery time period. A drying function unit is additionally provided and can be activated in time-separated manner with respect to the delivery function unit in order to free the dosing chamber from liquid residues.

2 Claims, 2 Drawing Sheets

MICRODOSING DEVICE

FIELD OF THE INVENTION

The invention relates to a microdosing device with a dosing chamber for the at least temporary reception of a liquid quantity and with which is associated at least one discharge opening, as well as with a vibrating unit, which is in operative connection with at least one boundary surface of the dosing chamber, in order to vibrate the same for a discharge process and with a delivery function unit connected to the vibrating unit for activating the latter during a delivery time period.

BACKGROUND OF THE INVENTION

Such a microdosing device is known from U.S. Pat. No. 6,196,219 B1. The known microdosing device has an atomizing unit in which is provided a dosing chamber for receiving a liquid quantity to be delivered. The dosing chamber is closed on one side by a membrane provided with several discharge openings in the form of perforations. With the facing boundary surface is associated a piezoelectric actuator serving as a vibrating unit. Into the dosing chamber issues a supply channel, which guides the liquid quantity required for a discharge process from a larger storage reservoir into the dosing chamber. During an activation of the vibrating unit, i.e. the piezoelectric actuator, the boundary surfaces of the dosing chamber and preferably also the membrane vibrate, so that the liquid quantity in the dosing chamber is atomized through the discharge openings of the membrane and consequently discharged. Even after the end of the actual discharge process the piezoelectric actuator continues to operate in order to heat the dosing chamber and thereby bring about a drying and evaporation of any liquid residues left behind.

EP 682 570 B1 discloses a further dosing device in which the liquid is delivered to the outside as an atomized spray mist through a perforated membrane from a storage area, in that the membrane is vibrated by vibrating means. Also in the case of this dosing device the vibrating means are operated longer than the time necessary for delivering the dosed liquid quantity. This is intended to deliver from the storage area the entire liquid quantity.

The problem of the invention is to provide a microdosing device of the aforementioned type permitting a precisely time-defined dosing of a liquid quantity.

SUMMARY OF THE INVENTION

This problem is solved in that additionally a drying function unit is provided, which is activatable in time-separated manner from the delivery function unit in order to free the dosing chamber from liquid residues. As a result of the time separation of the delivery function and the drying function a clearly time-defined dosability of the corresponding liquid is ensured. As a result it is possible to keep preferably at the same level the dosing volume over the time interval of the delivery function, so that a highly precise dosing is possible. There is no lagging of the vibrating unit, as is the case in the prior art. The solution according to the invention is particularly suitable for pharmaceutical applications which may require highly precise applications or administrations. The solution according to the invention is in particular also usable for cosmetic purposes or for perfuming mobile and stationary areas. According to the invention, the drying function is performed in time-displaced manner with respect to the application period, so that any liquid residues which have passed to the outside during the drying process no longer enter the human body and are instead preferably given off to the environment. Preferably the vibrating unit operates with ultrasonic waves, in that a piezoelectric actuator is excited with a corresponding frequency. The vibrating unit can also have actuators, which operate with different excitation vibrations or waves.

The solution according to the invention is particularly advantageously usable in the case of highly concentrated, pharmaceutical substances, in which even minor overdoses can have disadvantageous consequences for the human body, or where harmful contaminations of the liquid can arise. The drying function unit can either, as also the delivery function unit, be connected to the vibrating unit and act on the same, or can be designed as a functional mechanism completely independent of the vibrating unit. The inventive solution is particularly suitable for a microdosing device having an atomizing function in which the liquid quantity is discharged as an atomized spray mist through minute discharge openings in a membrane. In the same way the inventive microdosing device is also usable for other types of microdosing pumps, where there is no atomized liquid discharge.

According to a development of the invention the drying function unit is connected to the vibrating unit in order to activate the same for a drying process. This construction is particularly advantageous if a piezoelectric actuator is used as the vibrating unit. Thus, in the case of a suitable vibration frequency on the at least one boundary surface of the dosing chamber, it is possible to heat the latter and this leads to an evaporation of any liquid residues left behind.

According to another development of the invention the delivery function unit and drying function unit are parts of a common electronic control device, which is preferably provided with a time function element for coordinating the time-separated activation processes of the vibrating unit by the delivery function unit and the drying function unit. The integration of the delivery function unit and drying function unit in an electronic control device permits a particularly small construction. However, it is still possible to obtain highly precise switching or activation processes, more particularly of the piezoelectric actuator. The time function element ensures the time separation between the delivery function and the drying function. Preferably the drying function takes place at a later time than the delivery function.

According to a further development of the invention with the dosing chamber is associated a collecting reservoir for receiving liquid residues from the dosing chamber in gaseous or liquid state. This construction prevents the uncontrolled delivery of liquid residues into the ambient air. The collection of the liquid residues in the collecting reservoir permits an extremely clean disposal of such liquid residues. There can optionally also be a reuse of the collected liquid residues.

According to a further development of the invention the drying function unit incorporates a heating device or a delivery device for pumping or sucking out the liquid residues. These constructions form for the drying function unit functional mechanisms independent of the delivery function unit and which can be used as desired as a function of the intended use.

The invention also relates to a method for dosing small liquid quantities by the vibration of at least one boundary surface of a dosing chamber by means of the activation and deactivation of a vibrating unit.

Thus, the problem of the invention is also the creation of such a method permitting a particularly precise dosage, particularly for multiple applications.

This problem is solved in that the vibrating unit for a delivery time period for the discharge of the predetermined liquid quantity undergoes activation and then deactivation and that following the deactivation of the vibrating unit liquid residues which have been left behind in the dosing chamber are removed therefrom by a drying process. The method according to the invention is particularly suitable for the delivery of liquid in the form of atomized spray mist. As a result of the inventive solution a particularly accurate and time-defined dosing can be obtained. As a result of the independent and preferably complete drying of the dosing chamber prior to a further liquid discharge, precise dosings can take place when multiple applications occur. This avoids contamination of a new dosing quantity by liquid residues from the previously discharged dosing quantity. According to the invention it is important to bring about a good drying in the areas of the dosing chamber where a contamination risk may arise. A complete drying in the sections remote from these vital areas is not absolutely necessary.

BRIEF DESCRIPTION OF THE DRAWINGS

Further advantages and features of the invention can be gathered from the following description of preferred embodiments of the invention, the claims and the attached drawings, wherein show:

DETAILED DESCRIPTION OF THE INVENTION

Figure 1:
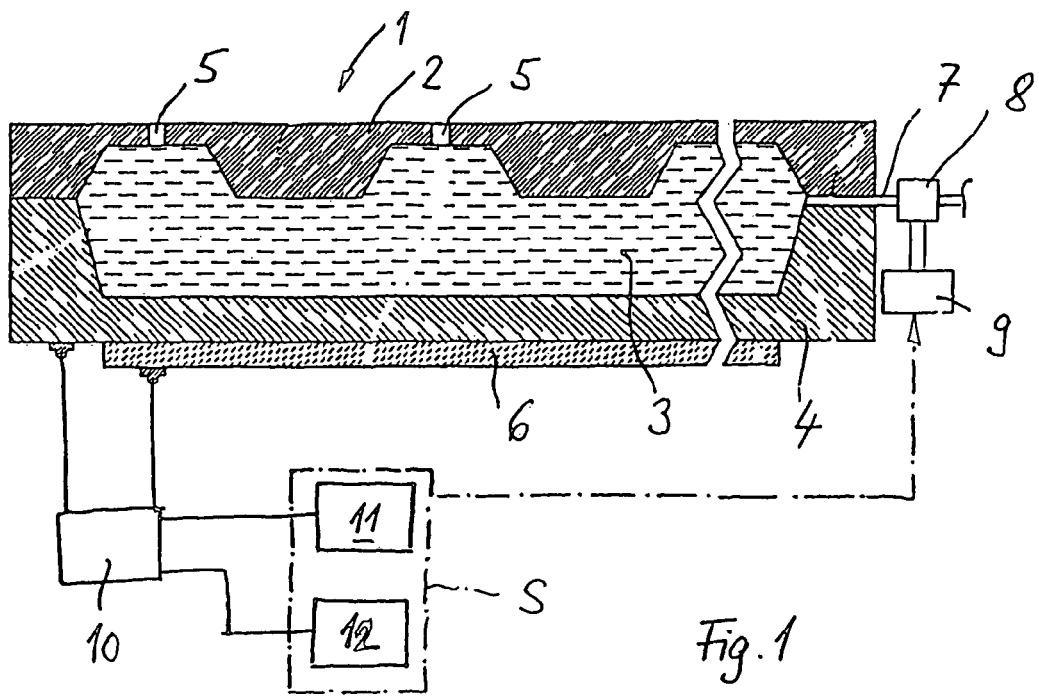
FIG. 1 Diagrammatically in a sectional representation an embodiment of a microdosing device according to the invention in the form of an atomizing unit.

A microdosing device according to FIG. 1 is constructed as an atomizing unit and corresponds to the basic structure of the microdosing unit known from U.S. Pat. No. 6,196,219 B1. The atomizing unit 1 is part of a medical inhaler, in order to introduce via the respiratory tracts into the human body liquid pharmaceutical agents. However, the atomizing unit can also be used for other application purposes and in other application fields. For supplementary disclosure of the basic structure of the atomizing unit reference is made to the content of U.S. Pat. No. 6,196,219 B1.

The atomizing unit 1 has a dosing chamber 3, which is bounded at the top by a membrane 2 and at the bottom by a base structure 4. The base structure 4 is preferably made from glass, metal, ceramic, silicon, a piezoelectric crystal, a highly compressed polymer or the like. The membrane 2 for the dosing chamber 3 serving as a cover structure is preferably made from plastic, ceramic, metal, silicon or the like. The membrane 2 has numerous minute discharge openings 5 in the manner of an areal perforation and they open the dosing chamber 3 to the environment. At least in the vicinity of the nozzle-like discharge openings 5, the membrane 2 is preferably made from silicon. The membrane 2 and base structure 4 are preferably circumferentially interconnected in order to obtain a closed dosing chamber 3.

On an underside of the base structure 4 is provided a piezoelectric actuator 6. In the connecting area between the membrane 2 and the base structure 4 is provided a supply channel 7 issuing into the dosing chamber 3 and with which is associated a microvalve 8 for opening and closing the supply channel 7. The microvalve 8 can be subject to the action of an actuating member 9, which is controlled by an electronic control unit S.

In not shown manner the supply channel 7 is connected to a liquid storage chamber. The dosing chamber 3 preferably has a capacity of 2 to 3 µl. The supply of liquid from the storage chamber to the dosing chamber 3 preferably takes place either by a slight overpressure in the vicinity of the storage chamber and/or by capillary action.

In the vicinity of each discharge opening 5, the dosing chamber 3 has a cavity conically tapering in the discharge direction. The discharge openings 5 have in each case a cylindrical wall. The diameters of the discharge openings 5 are significantly smaller than the diameters of the conical cavities at the transition of each frustum-shaped portion to the cylindrical discharge opening 5.

Figure 2:
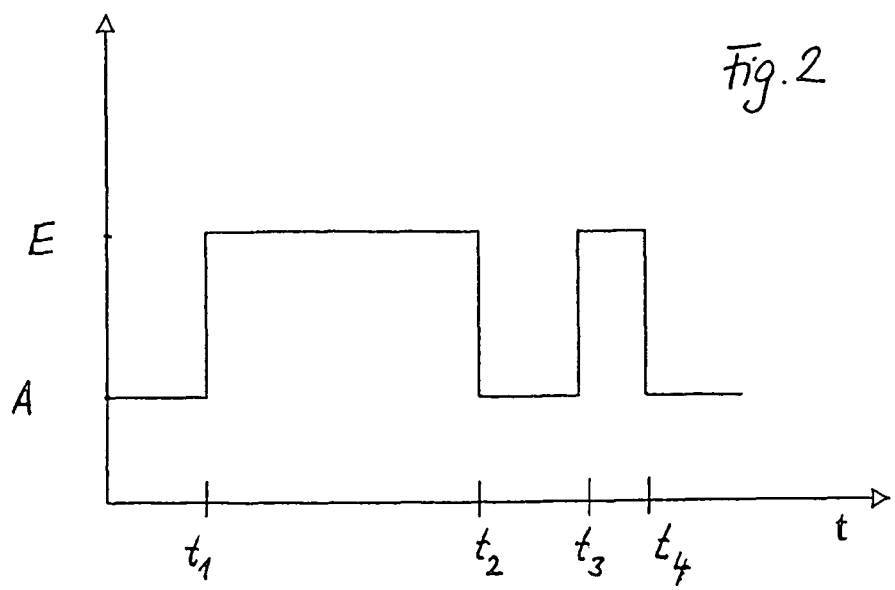
FIG. 2 A block diagram for the functional of the atomizing unit according to FIG. 1.

In order to permit a discharge process, the lower boundary surface of the dosing chamber 3, in the present case the base structure 4, can be vibrated, preferably in the high frequency range, by a piezoelectric actuator 6, which has a plate-like construction and is connected by an electrode to an electrical or electronic control element 10. The electrical or electronic control element 10 is connected by a further electrode to a base side of the base structure 4. The control element 10 is connected both to a delivery function unit 12 and to a drying function unit 11. Both the drying function unit 11 and the delivery function unit 12 form part of a diagrammatically represented electronic control unit S, which by means of a not shown time function element alternatively permits an activation of the control element 10 by the delivery function unit 12 or the drying function unit 11. Preferably both the drying function unit 11 and the delivery function unit 12 are designed as suitable electronic components. It is alternatively possible to create the drying function unit 11 and delivery function unit 12 within a software structure in an electronic subassembly so as to constitute separate function units. Both the drying function unit 11 and delivery function unit 12 are designed in such a way that they alternatively switch on and then switch off again for a certain time period the control element 10 and therefore the piezoelectric actuator 6. The block diagram of FIG. 2 illustrates the time-dependent switching on and off of the delivery function unit 12 and drying function unit 11. The reference letter A designates the switched off, i.e. deactivated state of the piezoelectric actuator 6 and E designates the switched on and therefore activated state of the piezoelectric actuator 6. On the abscissa of the planar coordinate system appears the time t. As has already been described, the ordinate represents the activating or operating state of the piezoelectric actuator. In the time period from t1 to t2 the actuator 6 is activated by the delivery function unit 12. During this time the dosing volume necessary for a corresponding application or administration is atomized and supplied to the corresponding respiratory tracts of the human being. The dosing volume is preferably between 10 and 30 µl. During the atomizing process in the time period t1 to t2 the microvalve 8 is opened by means of the actuating member 9. As from the time t2 and up to a time t3 the piezoelectric actuator 6 is switched off, i.e. deactivated. In order to remove any small liquid residues which may be present within the dosing chamber 3 before a corresponding liquid quantity is again supplied via the supply channel 7 and microvalve 8, as from time t3 the piezoelectric actuator 6 is activated, i.e. switched on by the drying function unit 11. As the base structure 4 and membrane 2 substantially dry vibrate due to the activation of the piezoelectric actuator 6, the dosing chamber 3 is subject to heating, so that any liquid residues present evaporate and are discharged through the discharge openings 5. The drying function unit 11 activates the piezoelectric actuator 6 up to the time t4 and then switches it off, i.e. deactivates it. Now once again a liquid quantity can be supplied from the storage chamber to the dosing chamber 3. A contamination of the liquid supplied from the closed storage chamber as a result of liquid residues remaining from the preceding dosing process is avoided, because such liquid residues are removed by the prior drying process. Now a further dosing process can take place, which once again leads in time-separated manner to a corresponding drying process.

Figure 3:
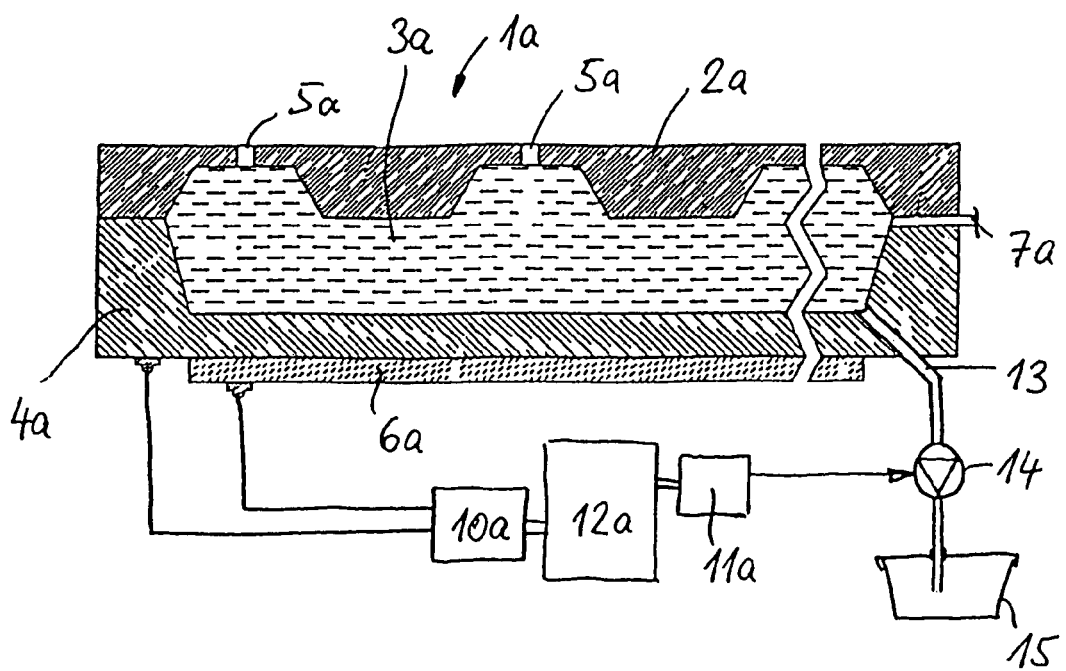
FIG. 3 Another microdosing device similar to FIG. 1, also in diagrammatic sectional representation.

The atomizing unit 1a according to FIG. 3 essentially corresponds to the atomizing unit 1 described relative to FIGS. 1 and 2, so that hereinafter reference will only be made to the differences. The essential difference in the atomizing unit 1a according to FIG. 3 is that the removal of any remaining liquid residues after a dosing process does not take place by reactivating the piezoelectric actuator 6a, but instead by activating a separate drying function unit 11a, which incorporates a suction device 14. Parts with the same function or construction have the same reference numerals as for the atomizing unit according to FIG. 1 and merely to facilitate understanding have been supplemented by the reference letter a. In addition to the elements or sections with the same construction as for the atomizing unit 1, in the base structure 4a is provided a suction channel 13, which commences in the base area of the dosing chamber 3a, passes out of the same through the base structure 4a and issues into a collecting reservoir 15. With the suction channel 13 is associated a suction pump 14, which is preferably designed as a micropump. The micropump 14 is activated by the drying function unit 11a, which is preferably designed as an electronic function or control component in accordance with FIG. 1 and by means of a not shown time function element functions in time-displaced manner with respect to the activation and deactivation of the delivery function unit 12a. An activation and deactivation diagram for the function of the atomizing unit 1a is provided in FIG. 2. Following the end of the dosing process the drying function unit 11a activates the micropump 14, which produces a vacuum in the dosing chamber 3a and in this way sucks off through the suction channel 13 any liquid residues present and removes same into the closed collecting reservoir 15.

The invention claimed is:

1. A method of operating a microdosing device having a dosing chamber for the at least partial reception of a liquid quantity and with which is associated at least one discharge opening, a vibrating unit in operative connection with at least one boundary surface of the dosing chamber in order to vibrate the same for a discharge process, a delivery function unit, connected to the vibrating unit, for activating the latter during a delivery time period, and a drying function unit for removing liquid residues from the dosing chamber, configured for activation in time-separated manner with respect to the delivery function unit, wherein the delivery function unit and drying function unit are parts of a common electronic control device provided with a time delay unit for coordinating the time-separated activating processes of the delivery function unit and the drying function unit, the method comprising the steps of:
    activating the delivery function unit to dispense a medium;
    activating the time delay unit for a pre-determined time-separation; and
    activating the drying function unit for a drying process.

2. The method according to claim 1, wherein the drying function unit is connected to the vibrating unit and further comprising the step of activating the vibrating unit for the drying process.

* * * * *